United States Patent [19]
Larson et al.

[11] Patent Number: 5,540,876
[45] Date of Patent: Jul. 30, 1996

[54] GAMMA RADIATION TREATED MATERIAL

[76] Inventors: Peter M. Larson, 2395 Charles St., Bexley, Ohio 43209; Lester M. Larson, 18626 Spanish Garden Dr., No. 342, Sun City West, Ariz. 85375

[21] Appl. No.: 462,585

[22] Filed: Jun. 5, 1995

Related U.S. Application Data

[63] Continuation of Ser. No. 89,729, Jul. 9, 1993, Pat. No. 5,378,531.

[51] Int. Cl.$^6$ ........................................ B06B 1/02
[52] U.S. Cl. .................. 264/479; 264/343; 264/473; 264/488
[58] Field of Search ........................ 264/479, 488, 264/473, 343

[56] References Cited

U.S. PATENT DOCUMENTS

| | | | |
|---|---|---|---|
| Re. 30,541 | 3/1981 | Larson | 128/90 |
| 3,490,444 | 1/1970 | Larson | 128/90 |
| 4,006,542 | 2/1977 | Larson | 161/112 |
| 4,122,137 | 10/1978 | Bohm | 264/22 |
| 4,144,223 | 3/1979 | Kent | 260/887 |
| 4,175,177 | 11/1979 | Potts | 528/354 |
| 4,221,253 | 9/1980 | Sieberling | 428/492 |
| 4,240,415 | 12/1980 | Wartman | 418/492 |
| 4,246,391 | 1/1981 | Watson, Jr. | 528/49 |
| 4,316,457 | 2/1982 | Siegeors | 428/492 |
| 4,340,497 | 7/1982 | Knopf | 252/188.3 R |
| 5,316,545 | 5/1994 | Cherubini | 602/7 |
| 5,415,623 | 5/1995 | Cherubini | 602/7 |

FOREIGN PATENT DOCUMENTS

| | | | |
|---|---|---|---|
| 746291 | 11/1966 | Canada | 128/19 |
| 934626 | 10/1973 | Canada | 128/40 |

OTHER PUBLICATIONS

Charlesby, A., "How Radiation Affects Long–Chain Polymers", *Nucleonics Journal*, vol. 12, pp. 18–25 (Jun. 1954).

*Primary Examiner*—James J. Bell
*Attorney, Agent, or Firm*—Connolly & Hutz

[57] ABSTRACT

Materials and items made of thermoplastic polyesters, such as poly (epsilon-caprolactone), synthetic rubber, such as Transpolyisoprene and Neoprene, and natural rubber, such as balata have improved properties when subjected to gamma radiation in the range from 0.5 to 30 megarads.

9 Claims, 2 Drawing Sheets

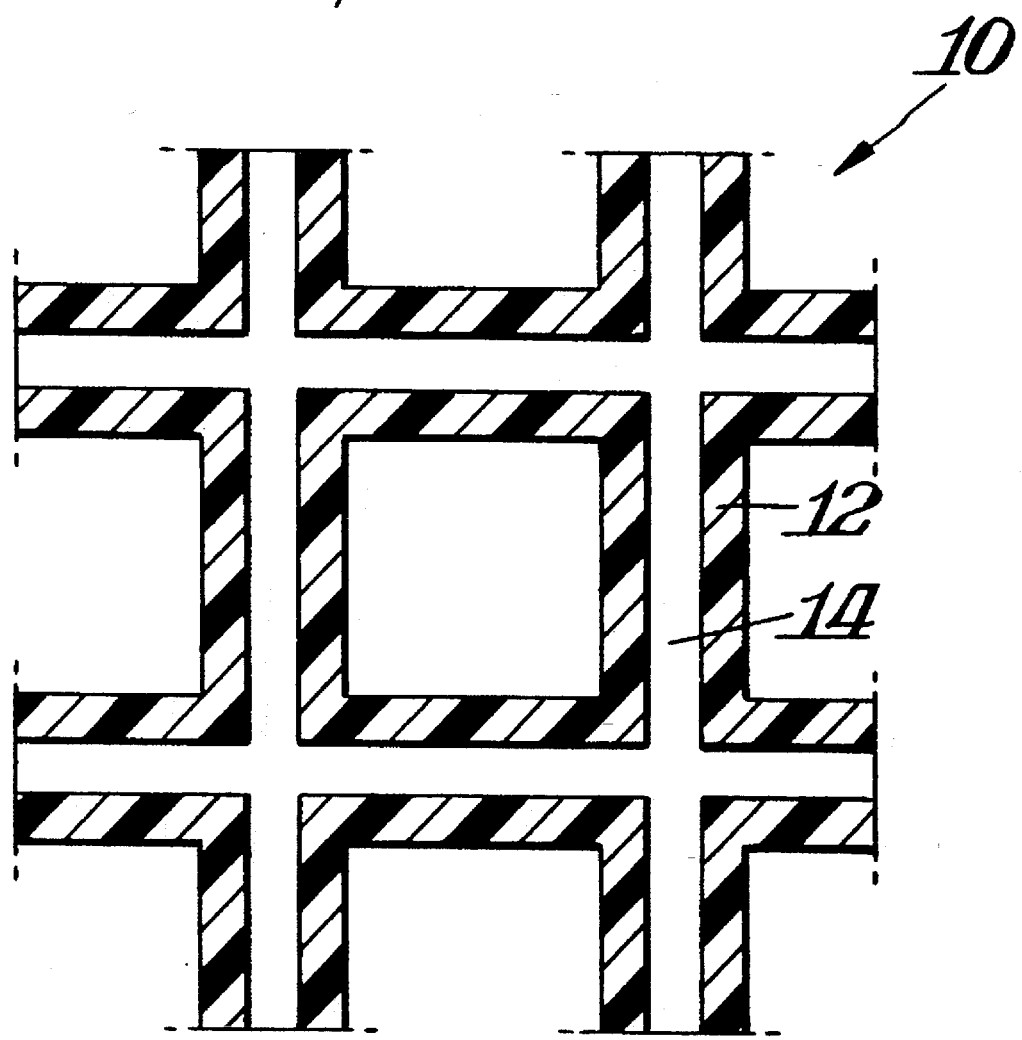

GAMMA RADIATION TREATED MATERIAL

This application is a continuation of PCT/US94/07409 Jul. 1, 1994 and a continuation of 08/089,729 Jul. 9, 1993 U.S. Pat. No. 5,378,531.

BACKGROUND OF THE INVENTION

This invention relates to improved properties of materials for making body supporting splints, casts, brassieres, belts, athletic supporters, headphones, ear plugs, impression casting material for dentists, masks, models, art molds, toys, golf balls, tires and other plastic and rubber items, including moldable items storable in rolls, stacks or sheets or moldings from which individual moldable elements are readily separated and formed into shapes for such uses as listed.

Plastic materials have been successfully used in the past for making splints, casts and the like. U.S. Pat. No. 3,490,444 describes the use of thermoplastic polydienes like transpolyisoprene and transpolychloroprene which melt between 60° C. and 100° C. and harden by crystallization at about 40° C. whereby this can be formed for use as a body supporting member. An important feature of that invention is the incorporation of a filler (e.g. short lengths of fiber) such that the final product would be free of substantial creep or deformation under long periods of use below about 40° C. Other polymers melting between 50° C. and 110° C. and hardening by crystallization have also been recommended. U.S. Pat. No. 3,604,413 recommends copolymers of trioxane and several other polymers. Poly (epsilon-caprolactone)(PCL) has also been found to be an excellent splint or cast material (U.S. Pat. No. 4,144,223). Polyurethanes based on prepolymers of poly (epsilon-caprolactone) have also been used (U.S. Pat. No. 4,316,457).

As described in earlier patents, the polymers can be heated in hot water at a temperature usually exceeding 50° C. and up to about 100° C., whereby they become soft, self-adherent and pliable sufficient to be deformed and shaped as a cast or splint or protective device. When allowed to cool in air to about 40° C., the materials remain pliable, moldable and cohesive for a period of several minutes, exhibiting a hysteresis, as described in U.S. Pat. No. Re 30,541. During this time the splint, cast or device can be molded directly to the patient without discomfort, whereupon the so shaped plastic hard sets by crystallization to assume a rigid form as a useful body support member or protective device.

Poly (epsilon-caprolactone) is an excellent splint or cast material by itself and in blends with common, fine particle size fillers and pigments, such as silica, diatomaceous earth, clay, and titanium dioxide. The filler may be present in the blends at a concentration of from about 1 to about 30 parts by weight per 100 parts by weight of the poly (epsilon-caprolactone). Mixtures of the fillers may also be used, especially of silica and titanium dioxide, which impart a desirable white color to the compound.

Poly (epsilon-caprolactone) (PCL) makes an excellent cast or splint, in the hardened state. However, the heat-softened material is difficult to handle because it is fluid and sticky. This can be overcome by adding reinforcing fibers, cheesecloth (to support the plastic), or by blending PCL with a polymer like Transpolyisoprene (TPI), which is more elastic in the heat softened state.

Applicant Lester Larson has conducted laboratory investigations of the properties of PCL-TPI blends. The stickiness of heat-softened PCL disappears at around 50—50 mixtures, but other properties (e.g. tensile strength) are better when 75 % or more of the blend is Transpolyisoprene. Pure PCL is good in respect to hardness, strength, hysteresis, and it has the advantage of being transparent in the heat-softened state. Fluidity and stickiness are its drawbacks. It has been found that this softened state fluidity is reduced by electron radiation of thin sheets of the polymer (U.S. Pat. No. 4,240, 415).

U.S. Pat. No. 4,144,223 demonstrates blends containing 50 to 98 parts by weight of Transpolyisoprene along with 2 to 50 parts by weight of Poly (epsilon-caprolactone), for use as medical splints and as golf ball covers. It further mentions the need to vulcanize or "cure" such a blend for use as a golf ball cover.

Gamma radiation is commonly used as a sterilization method for hospital items such as catheters, surgical items and critical care tools. Gamma radiation is also commonly used to kill bacteria in commercially sold items such as pacifiers, nipples, baby bottles, and even food items such as strawberries, chicken, and dog food. Safe techniques for using gamma radiation are well understood and in common use at licensed sterilizing facilities throughout the United States and other industrialized countries.

SUMMARY OF THE INVENTION

An object of this invention is to provide techniques for using gamma radiation to produce materials usable as orthopedic splints, casts, shoe inserts, arch supports, masks, models, art molds, dental molds, golf ball covers, balls, toys, tires, and other items. We have found that Gamma radiation has advantages over electron radiation and over conventional chemical means for the "curing" or "cross-linking" of plastic such as poly (epsilon-caprolactone), synthetic rubber such as Transpolyisoprene and Neoprene, and natural rubber such as balata.

A further object of this invention is to provide techniques which improve upon those using electron radiation such as in U.S. Pat. No. 4,240,415.

Gamma radiation is different in kind from electron radiation. Beta rays (electron beams) interact with matter and transfer energy by collision. High speed electrons undergo relativistic effects and as they approach the speed of light, the electron mass approaches infinity. Gamma rays (x-rays) travel at the speed of light and interact with matter by resonance (they have 0 mass).

In this particular application the gamma radiation process has several advantages. Whereas electron beams penetrate most matter only a few millimeters and can only be used on thin items or items of low density, gamma radiation is very penetrating. Much thicker mass can be treated. Stacks of plastic sheets 12 or more inches thick can be uniformly radiated by conventional means (e.g. using cobalt 60). Also, gamma radiation can be used on shaped objects, such as precut or preformed splints, customized supports like arch supports and shoe inserts, preformed masks, models, or art molds, on packaged items, such as boxes of golf balls, and on larger items such as bicycle tires and automobile tires, which can be mechanically transported around a cobalt 60 source.

Gamma radiation can be applied to pre-boxed or prepackaged materials and items packaged in bulk quantities. Having materials prepackaged makes for easier handling and processing, and additionally, since gamma radiation in effect sterilizes these materials, packaged items can remain essentially sterile until they are unwrapped by the end-user. This is especially useful in medical applications. The gamma radiation process is also less expensive than electron radiation for bulk items. Commercial operations are well understood and are now being used (by us) for these purposes.

THE DRAWINGS:

FIG. 3 is a cross-sectional view of a sheet formed in accordance with this invention.

DETAILED DESCRIPTION

The following examples illustrate the operation and practice of this invention:

EXAMPLE 1

Sheets of poly (epsilon-caprolactone) ⅛" thick were subjected to dosages of 0, 5, 10, 20, and 40 megarads of gamma radiation. The sheets were then cut into strips 6"×½"×⅛. These strips were then dipped in hot water (at 160° F.) until they became fully softened and transparent (about 25 seconds), whereafter they were manipulated manually by pulling, stretching, bending, and forming into various shapes and allowed to cool and harden at room temperature.

Unradiated (0 megarads) PCL strips showed no resistance to pulling, when heated. Radiated strips developed a resistance to pulling, directly in proportion to the amount of radiation dosages. This resistance is best described as an "elasticity", because the radiated strips tended to pull back to their original form when stretched.

Figure 1:
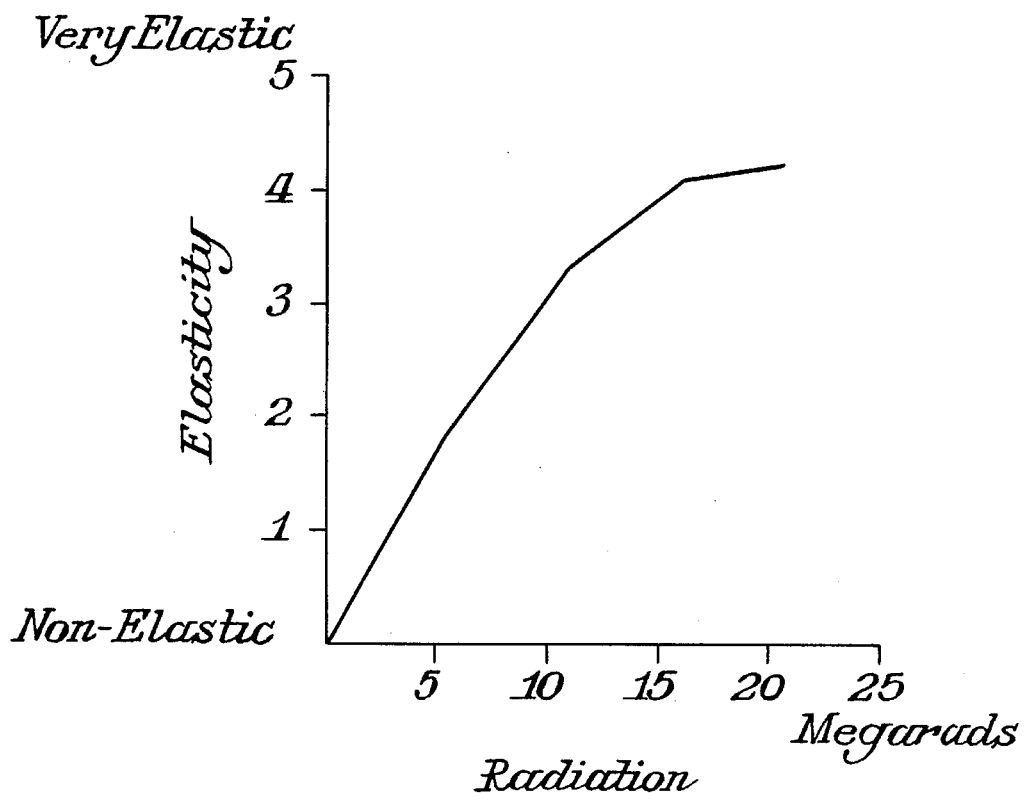
FIG. 1 is a graph showing elasticity properties with respect to gamma radiation.

FIG. 1 illustrates the observed elasticity.

Elasticity at level 0 means no observable elasticity when heated, as in unradiated samples. Unradiated strips could be stretched out with little to no resistance and had no tendency to pull back to their original shape. If stretched out, even slightly, they became almost liquid and would drip to the floor. Strips radiated at 5 megarads had a slight tendency to pull back to their original shape when stretched, and would not drip to the floor. 10 and 20 megarad strips became progressively more difficult to stretch out, would not break off when stretched excessively, and if reshaped, would hold their reshaped configuration. Strips radiated at 40 megarads could not be lengthened. If pulled with an excess of at 25 pounds they would stretch less than 25 % and break in two, with the ends snapping back to their original shape.

All samples showed no evidence of internal gassing as described from electron radiation in U.S. Pat. No. 4,240,415.

EXAMPLE 2

Sheets of polyurethanes based on prepolymers of poly (epsilon-caprolactone) are prepared as per U.S. Pat. No. 4,316,457 with a melting point of about 55° C. The material is extruded into sheets 24"×18"×⅛" which are subjected to dosages of 0, 5, 10, 20, and 40 megarads of gamma radiation. The sheets are then cut into strips 6"×½"×⅛". These strips are then dipped in hot water (at 160° F.) until they become softened, whereafter they are manipulated manually by pulling, stretching, bending, and forming into various shapes and allowed to cool and harden at room temperature.

Unradiated (0 megarads) strips show little to no resistance to pulling when heated and are too fluid to manipulate into shapes. Radiated strips develop a resistance to pulling, directly in proportion to the amount of radiation dosages. This resistance is best described as an "elasticity", because the radiated strips tend to pull back to their original form when stretched. The amount of elasticity induced by the radiation is measured to be similar to the elasticity induced in the strips of pure poly (epsilon-caprolactone) as in example 1.

EXAMPLE 3

Blends of poly (epsilon-caprolactone), silica and titanium dioxide were prepared in a mixture of 100 parts PCL to 20 parts silicon dioxide and 3 parts titanium dioxide. The mixture was extruded into sheets 24"×18"×⅛" which were subjected to dosages of 0, 5, 10, 20, and 40 megarads of gamma radiation. The sheets were then cut into strips 6"×½"×⅛". These strips were then dipped in hot water (at 160° F.) until they became fully softened (about 25 seconds), whereafter they were manipulated manually by pulling, stretching, bending, and forming into various shapes and allowed to cool and harden at room temperature.

Unradiated (0 megarads) strips showed no resistance to pulling, when heated. Radiated strips developed a resistance to pulling, directly in proportion to the amount of radiation dosages. This resistance is best described as an "elasticity", because the radiated strips tend to pull back to their original form when stretched. The amount of elasticity induced by the radiation was measured to be identical to the elasticity induced in the strips of pure poly (epsilon-caprolactone) as in example 1.

EXAMPLE 4

Sheets of poly (epsilon-caprolactone) 18"×24"×⅛" were dipped in hot water (at 160° F.) until they became somewhat softened (about 20 seconds), whereafter they were cut and formed to the shape of shoe inserts and arch supports, allowed to cool, and packed in boxes, 12 units per box. These boxes were then mechanically transported around a cobalt-60 source and radiated with gamma radiation at a level of 5 megarads, as measured by strategically placed dosimeters. Thereafter the shoe inserts and arch supports were removed from the boxes and custom fitted to users' feet by heat softening the inserts and arch supports with a hot air gun, allowing to cool for about two minutes, and then molding directly to the contours of the wearer's foot, and holding in place for about three minutes, until the material hardened. When heated, the inserts and arch supports displayed a "shape memory" and did not flatten out or lose the consistency of their thickness. Detailed adjustments were made by reapplying heat with a hot air gun directed at the specific spot to be adjusted, manually reshaping the spot and holding in place until the material hardened again.

Unradiated poly (epsilon-caprolactone) shoe inserts were tried in the same manner. However, when they were softened with a hot air gun for application to the wearer's foot, the plastic lost its shape, became inconsistent in thickness, became drippy, and was difficult to control.

EXAMPLE 5

Sheets of poly (epsilon-caprolactone) 18"×24"×⅛" were placed in boxes, 20 sheets per box and mechanically transported around a cobalt-60 source and radiated with gamma radiation at a level of 5 megarads, as measured by strategically placed dosimeters. The sheets were then unpacked and individually dipped in hot water (at 160° F.) until they became fully softened (about 20 seconds), whereafter they were removed from the water and allowed to cool in room air. After about two minutes, the sheets became comfortable to touch. Twelve inch circular pieces were then cut out for making masks, with a hole cut out to allow breathing. Pieces were draped directly over a person's face and gently pressed against the facial contours. The mask was held in place for approximately three minutes, until it hardened. The mask was then painted.

A similar procedure was used to create artistic molds of hands and other body parts.

Unradiated poly (epsilon-caprolactone) sheets were tried in the same manner. However, when they were softened for application the sheets lost their shape, became inconsistent in thickness, became drippy, and were difficult to control, especially around angular facial features like the nose and jaw.

EXAMPLE 6

100 PCL sheets 18"×24"×⅛" were packaged in boxes (4 sheets per box); those boxes placed together in a mechanical carder and conveyed around a cobalt-60 source until a uniform dosage of 10 megarads of gamma radiation was achieved, as measured by dosimeters strategically placed on the packages. Sheets were then removed, heat softened, cut to shape and formed into a variety of orthotic splints, and applied to patients by professional medical therapists.

EXAMPLE 7

Three preformed "cock-up" wrist splints made from ordinary PCL ⅛" thick sheets which had not been irradiated were placed in a cardboard box and subjected to cobalt 60 gamma rays until strategically placed dosimeters indicated a uniform dosage of 10 megarads. These irradiated "preforms" were then heat softened and fitted closely to a patient's wrist by conventional heat softening, fitting and cooling to hardness. This procedure enabled the therapist to form and customize the splint quickly and easily by reshaping the "preform" instead of having to start from a plain sheet, cutting and shaping it. Subtle adjustments to customize the fit of the "preform" were made without the material becoming liquid or losing it's basic shape. It was economical in that there is little or no waste of material. The preform needed little or no trimming.

EXAMPLE 8

Sheets of poly (epsilon-caprolactone) ⅛" thick were subjected to dosages of 0, 5, 10, 20, and 40 megarads of gamma radiation. The sheets were then cut into strips 6"×½"×⅛". These strips were then dipped in hot water (160° F.) until they became fully softened and transparent (about 25 seconds), whereafter they were manually stretched out to a length of 12 inches and allowed to cool and harden at room temperature, except for the 40 megarad strips which broke in two when stretched more than 25 % of their length. The strips were then reheated in the hot water, whereupon the radiated strips tended to quickly shrink back toward their original shapes, the amount of such tendency increasing in proportion to the radiation levels of the strips.

Unradiated strips showed no such "melt-memory" tendency, and did not shrink back upon reheating. Strips at 5 megarads returned to a length of approximately 9 inches. Strips at 10 megarads returned to within an inch of their original length, and strips at 20 megarads returned almost 100% to their original length and width. In all radiated strips this "melt-memory" displayed itself immediately as the samples were dipped in the hot water.

Figure 2:
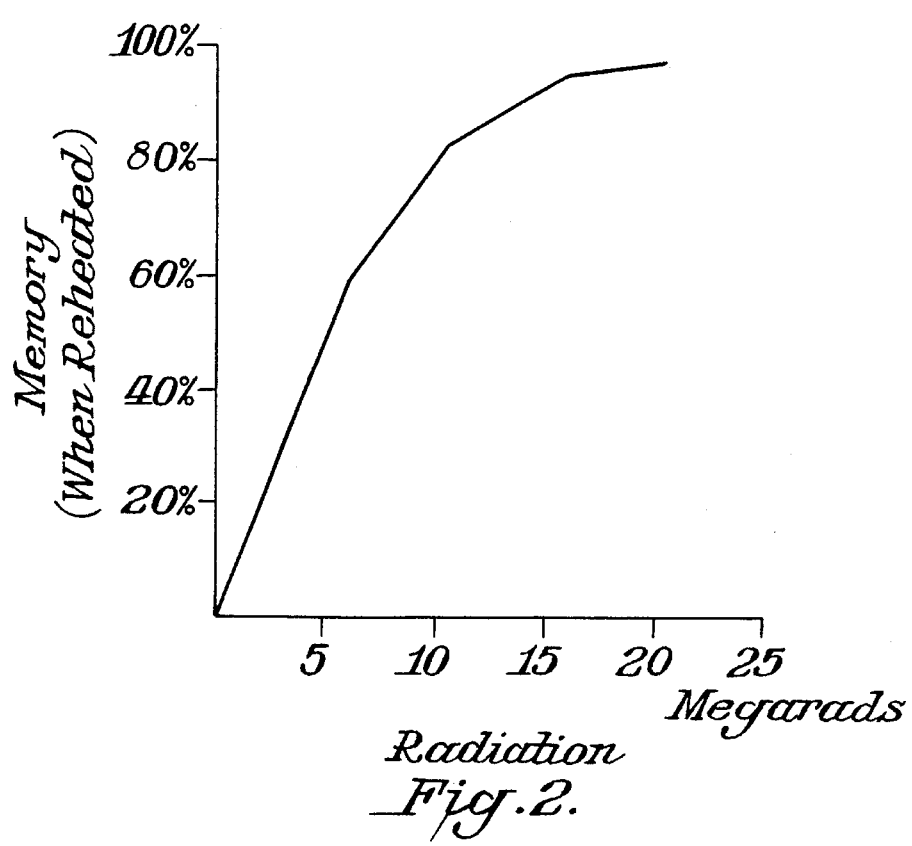
FIG. 2 is a graph showing memory properties with respect to gamma radiation.

FIG. 2 illustrates the melt memory for different levels of radiation.

EXAMPLE 9

A blend was prepared containing 100 parts by weight of Transpolyisoprene mixed with 20 parts silicon dioxide, 3 parts titanium dioxide and 2 parts Poly (epsilon-caprolactone). The material was rolled out into sheets 24"×18"×⅛" using a multi-roll calendaring mill. The sheets were then subjected to dosages of 0, 2, 5 and 10 megarads of gamma radiation. The sheets were then cut into carefully measured pieces 6"×4"×⅛", with the 6" axis cut in the direction of flow of the manufacturing mill. These pieces were then dipped in hot water (at 160° F.) until they became fully softened (about 30 seconds), removed from the water and allowed to cool to room temperature. Then the pieces were measured again. Unradiated pieces showed a significant shrinkage in width along with an expansion in length and depth. This deformation is a problem for the practical use of these sheets, in that excessive shrinkage and expansion make it difficult and often impractical to precut usable pieces before they are heated. This problem was overcome by "curing" the sheets with gamma radiation, as the following chart indicates:

| RADIATION LEVEL | LENGTH (INCREASE) | WIDTH (DECREASE) | DEPTH (INCREASE) |
| --- | --- | --- | --- |
| 0 MRADS | 12.5% | 5.9% | 6.8% |
| 2.5 MRADS | 2.9% | 0.9% | 1.9% |
| 5 MRADS | 1.1% | 0.7% | not measurable |
| 10 MRADS | 0.6% | 0.4% | not measurable |

EXAMPLE 10

Golf balls are made using standard industry practices, except that the covers are made of a 50/50 mixture of Transpolyisoprene and natural balata rubber, and have not been vulcanized or "cured". The balls are then placed in boxes and mechanically transported around a cobalt-60 source, until they have been radiated with gamma radiation at a level of 5 megarads, as measured by strategically placed dosimeters. The balls are then tested on a golf course and observed to perform the same as balls which have been vulcanized or "cured" using traditional chemical means.

EXAMPLE 11

Bicycle tires made of Neoprene rubber are manufactured using standard industry methods, except that no vulcanizing chemicals or vulcanization "accelerator" chemicals are mixed into the rubber. The unvulcanized tires are mechanically transported around a cobalt-60 source, until they have been radiated at a level of 8 megarads, as measured by strategically placed dosimeters. The tires are then put into use and observed to perform the same as tires that have been vulcanized by traditional methods.

These tires have an environmentally useful benefit in that they can be manufactured without potentially toxic chemical additives, such as vulcanizing chemicals. Such benefit is especially important after the tires have been used and must be disposed of or recycled.

EXAMPLE 12

It is known that certain polyesters can be cross-linked by ionizing radiation, particularly unsaturated polyesters in which the difunctional acid contains a double bond (e.g. derived from maleic, itaconic acid, etc.). In such materials, ionizing radiation initiates polymerization by forming free radicals which react with the double bonds in a way similar to the polymerization of a vinyl monomer.

The radiation dosage needed to effect cross-linking in poly (epsilon-caprolactone) can be reduced by incorporating certain additives. The effective additives are chemicals containing two or more double bonds in each molecule.

The incorporation of 2-Ethyl-2-(hydroxymethyl)-1-3-propanediol trimethacrylate at a level of 2% in poly (epsilon-caprolactone) reduces the dosage of gamma radiation required to cross-link the polymer by at least half. The incorporation of other polyunsaturated molecules, such as neoprene or butadiene rubbers is also observed to accelerate the cross-linking reaction.

EXAMPLE 13

Polymeric materials possessing crystallinity, i.e. regions of regular structure in which the polymeric chains are closely packed, exhibit melting points. The enthalpy of melting or the heat required to convert the solid polymer to the liquid state is a direct measure of the crystallinity present. Further, when the liquid solidifies upon cooling, the heat of crystallinity is released by the polymer to its environment.

Any physical or chemical change to the polymer which inhibits crystallinity will lead to a decrease in the enthalpy of melting. For instance, polymer chains with side groups sticking out from the chain are likely to be less crystalline than linear chains materials. Alternatively, if the polymer chains of a crystalline polymer are tied together or cross-linked, then it may require more energy to cause disruption of the ordered polymer chains.

Differential scanning calorimetry (DSC) is an instrumental methodology which measures the enthalpies of melting and crystallization very accurately. Hence, it is a reasonable analytical tool to use when looking at the effect of radiation induced cross-linking upon crystalline polymers.

Samples of poly (epsilon-caprolactone) radiated at 0, 10 and 40 megarads of gamma radiation were analyzed with DSC to measure the initial heat of melting for the samples; with the following results:

| Sample | 1st Heat Enthalpy |
| --- | --- |
| 0 mrads | 77 J/g |
| 10 mrads | 80 J/g |
| 40 mrads | 84 J/g |

These first of enthalpies show a measurable but limited increase with increased radiation. This is consistent with increasing but limited polymer cross-linking with increased dosage of gamma radiation.

EXAMPLE 14

This example had as its object to determine the effect of gamma radiation on medical splinting sheets made of poly (epsilon-caprolactone), a thermoplastic polyester having a melting point between 50° C. and 90° C.

METHOD:

Four sheets 12"×12"×⅛", of poly (epsilon-caprolactone) were repeatedly passed by a cobalt 60 source, until the following dosages were reached for each of the four sheets:

| Sheet #1 | 6.28 megarads |
| Sheet #2 | 11.50 megarads |
| Sheet #3 | 16.35 megarads |
| Sheet #4 | 20.15 megarads |

The sheets were then cut into one inch strips and melted one at a time in a hot water bath at 70° C. Strips were then manipulated, manually distorted into various shapes, and cooled to room temperature. Then they were reheated and manipulated again. Throughout this process, observations were made as to the tensile strength, stiffness, elasticity, moldability, and "memory" (i.e. the tendency to return to its original shape when reheated), for strips from each of the different sheets. Differences in the performance of the samples are then attributed to the effect of gamma radiation at the different levels. A control sample, which was given no radiation, was also used.

OBSERVATIONS:

The two most dramatic changes caused by the gamma radiation appear to be increased elasticity in the material's molten state, and "memory" when samples are reheated. First, elasticity:

When non-radiated strips are heated they become almost liquid. They can be stretched easily. They lose their shape immediately, and if a strip is held firmly at one end, the other end will drip all the way to the floor. Strips from sheet #1 however did not drip, could be stretched fairly easily, but had an elastic tendency to resist stretching to some degree. When heated, strips from #2 had a markedly stronger elasticity. They could be stretched, but only by pulling with some strength, and they had a tendency to return to their original shape unless held in the new position until the samples cooled and hardened. When heated, strips from #3 and #4 behaved almost identically. They displayed a little more elasticity than the #2 strips, and were a little tougher to stretch. However, the increased elasticity of #3 and #4 was slight, compared to the difference between #1 and #2.

"MEMORY":

When non-radiated sheets were heated, stretched and cooled, and then reheated, they exhibited no tendency to return to their original shape, i.e. no "melt-memory". When #1 strips were similarly treated, they quickly shrank back to their original shapes. The same was true for #2, #3, and #4 strips. They did seem to shrink back more quickly than the #1 strips, but even the #1 strips returned quickly to their original shape.

TENSILE STRENGTH:

When heated, non-radiated strips became almost liquid, with no tensile strength. #1 strips required a little pull to stretch them out when heated . . . #2 strips much more pull . . . and #3 and #4 strips were a little tougher yet, requiring some real strength to pull them out by hand. #3 and #4 were roughly identical in this area. In their cooled, hardened states, all samples, including the non-radiated samples exhibited extreme hardness, stiffness, and high tensile strength, i.e. they could not be stretched by hand.

MOLDABILITY:

Non-radiated pieces were very moldable when heated. However, their tendency to run and drip makes them less desirable for making splints. The runniness creates a "pizza dough" effect, leaving thin spots, and weak spots in molded pieces, unless the person doing the molding is very skilled and very careful. The "pizza dough" effect disappeared in the radiated samples. #1 strips were easy to mold into any shape when heated, but had a "flimsy" feel to them until they cooled and hardened. #2 strips had more tendency to spring back, and resisted molding a bit, but they hold their thickness more uniformly and had a good substantial feel, when pushed into a new shape. #3 and #4 strips were difficult to mold when heated. Their tendency to spring back made it almost impossible to give them a new shape, without having to grip them tightly all through the cooling process, till they hardened.

CONCLUSIONS:

The changes induced by gamma radiation are consistent with a conclusion that cross-linking has occurred in the poly (epsilon-caprolactone). It appears this cross-linking starts at a dosage less than 6 megarads, and reaches a saturation point somewhat around 15 megarads. This is obviously a rough estimate, based on the above subjective observations. This cross-linking is a substantial improvement in this material for the purpose of making medical splints and casts. By controlling the amount of gamma radiation, it will be possible to market a product (or Products) with a desired amount of moldability and memory. Because of the penetrating nature of gamma radiation, it should be possible to radiate sheets in bulk. This would be an economically advantageous process. An additional advantage is that gamma radiation would render the sheets sterile, an obvious benefit for their intended medical use.

FIG. 3 illustrates a sheet 10 in accordance with this invention. As shown therein the poly (epsilon-caprolactone) material 12 is coated on a substrate 14. Where the sheet 10 is used as an orthopedic cast, the substrate 14 may be a netting and the polyester 12 would be coated around each strand to form a foraminous sheet 10.

The invention may also be broadly practiced using the techniques described in U.S. Pat. No. 4,240,415 (the details of which are incorporated by reference thereto) except that gamma radiation would be used instead of electron radiation.

The advantageous properties of sheets produced by the invention may be used in a wide variety of products of otherwise conventional construction particularly for support purposes. Such products include orthopedic splints, casts, shoe inserts and arch supports. Other protective elements which make use of the invention include shoes, brassieres, belts, athletic supporters, headphones, ear plugs, and dental impression casting materials. The sheets of the invention may be moldable plastic storable in rolls, stacks or sheets or moldings from which individual moldable elements may be readily separated and formed into shapes.

What is claimed is:

1. A method of forming a support sheet comprising the steps of:

a) forming a preform sheet of poly (epsilon-caprolactone) of average molecular weight greater than about 5,000 having a melting point between about 50° C. and about 100° C.;

b) subjecting the sheet to gamma radiation in the range from about 0.5 to about 20 megarads;

c) heating the sheet, to its softening point, until it is melted or clear;

d) forming the sheet into a desired shape, and e) allowing the sheet to cool until hardened.

2. A method as recited in claim 1, wherein the sheet is comprised of a blend of poly (epsilon-caprolactone), containing up to about 30 parts of fine particle size fillers and/or pigments per 100 parts of poly (epsilon-caprolactone).

3. A method as recited in claim 1, wherein the sheet is comprised of a blend of poly (epsilon-caprolactone), containing up to about 30 parts of fine particle size fillers and/or pigments, selected from the group consisting of silica, diatomaceous earth, clay, and titanium dioxide per 100 parts of poly (epsilon-caprolactone).

4. A method as recited in claim 1, wherein the sheet is a polyurethane based on prepolymers of poly (epsilon-caprolactone).

5. A method as recited in claim 1, wherein the sheet contains a mixture of at least about 95% poly (epsilon-caprolactone), and an effective amount up to about 5% 2-ethyl-2-(hydroxymethyl)-1-3-propanediol trimethacrylate.

6. A method as recited in claim 1, wherein the sheet contains a mixture of at least about 90% poly (epsilon-caprolactone), blended with an effective amount up to about 10% neoprene, alkene, or other cross linking agents.

7. A method as recited in claim 1, wherein the support sheet is selected from the group consisting of orthopedic splints, casts, shoe inserts, arch supports, shoes, brassieres, belts, athletic supporters, headphones, ear plugs, dental casting materials, masks, art molds, golf balls, balls, toys, and tires.

8. A method as recited in claim 2, wherein the support sheet is selected from the group consisting of orthopedic splints, casts, shoe inserts, arch supports, shoes, brassieres, belts, athletic supporters, headphones, ear plugs, dental casting materials, masks, art molds, golf balls, balls, toys, and tires.

9. A method as recited in claim 4, wherein the support sheet is selected from the group consisting of orthopedic splints, casts, shoe inserts, arch supports, shoes, brassieres, belts, athletic supporters, headphones, ear plugs, dental casting materials, masks, art molds, golf balls, balls, toys, and tires.

* * * * *